United States Patent [19]

Hammond

[11] Patent Number: 4,622,400

[45] Date of Patent: Nov. 11, 1986

[54] PREPARATION OF CERTAIN M-AMINOPHENOLS AND THE USE THEREOF FOR PREPARATION OF LASER DYES

[75] Inventor: Peter R. Hammond, Livermore, Calif.

[73] Assignee: The United States of America as represented by the United States Department of Energy, Washington, D.C.

[21] Appl. No.: 566,924

[22] Filed: Dec. 29, 1983

[51] Int. Cl.$^4$ .................. C07D 215/20; C07D 215/36
[52] U.S. Cl. ................................. 546/179; 546/178; 546/181; 546/152; 546/148; 546/168; 549/359; 544/99
[58] Field of Search ............... 546/157, 151, 181, 178, 546/179

[56] References Cited

U.S. PATENT DOCUMENTS

| 2,268,443 | 12/1939 | Crowder | 546/157 |
|---|---|---|---|
| 3,933,828 | 1/1976 | Kano et al. | 546/157 |
| 4,042,697 | 8/1977 | Garside et al. | 546/151 |
| 4,218,448 | 8/1980 | Aldrich et al. | 546/157 |
| 4,349,554 | 9/1982 | Uematsu et al. | 546/157 |

FOREIGN PATENT DOCUMENTS

| 44792 | 9/1888 | Fed. Rep. of Germany | 564/305 |
|---|---|---|---|
| 48151 | 7/1889 | Fed. Rep. of Germany | 564/305 |
| 69074 | 5/1893 | Fed. Rep. of Germany | 564/305 |
| 750399 | 7/1945 | Fed. Rep. of Germany | |
| 1110576 | 9/1976 | Japan | 546/157 |

OTHER PUBLICATIONS

Morrison & Boyd (2nd ed) Organic Chemistry, Allyn & Bacon Inc; pp. 714 and 1088.
Allinger et al; Organic Chemistry, Worta Publish. 1971, p. 354.
Advanced Organic Chemistry; Reactions, Mechanisms & Structure, March, McGraw Hill Pub. (1968) Irsted pp. 401–402.
Jones, Quinolines, Wiley Publications, vol. 32, 89–90, Heterocylic Compounds (1977), pp. 51–52, 26–27, 89–90, 80–81, 64–67.
Flippen-Anderson et al., Acta Crystallogr., Sect. C; Cryst. Struct. Commun. 1984, C 40(6), 1065-8.
Kost et al., J. Gen. Chem. USSR (Eng.) 26, 1929 (1956), Reduction with Formic Acid and its Derivatives.
Hammond et al., J. Heterocyclic Chem., 12, 1061 (1975), 2-Keto-4-Trifluoromethyl-9-Methyl-6, 7, 8, 9-tetrahydro-2H-pyrano [3,2-g] Quinoline, An Efficient, Stable Laser Dye.
Braun, Chem. Ber. 47, 492 (1914), Untersuchungen uber Phenolbasen II.
Feer et al., Chem. Ber., 18, 2388 (1885), Ueber einige Derivate des Methylhydrochinolins.
Meisenheimer, Justus Liebigs. Ann. Chem., 385, 117 (1911), Optisch aktive Aminoxyde.
Barltrop et al., J. Chem. Soc. 108 (1951), A New Technique for the Reduction of Certain Heterocyclic Methiodides.
Bahner et al., J. Amer. Chem. Soc. 74, 4198 (1952), Derivatives of Tetrahydroquinoline and Tetrahydroisoquinoline.
Hünig et al., Justus Liebigs Ann. Chem. 592, 180 (1955), Farbe und Konstitution II—Polarisierbare Azofarbstoffe.
Gribble et al., Synthesis, 1970 (10) 650, Reactions of Sodium Borohydride in Acidic Media: III, Reduction and Alkylation of Quinoline and Isoquinoline with Carboxylic Acids 1,2.

Primary Examiner—Albert T. Meyers
Assistant Examiner—D. L. Dinner
Attorney, Agent, or Firm—Clifton E. Clouse, Jr.; Roger S. Gaither; Judson R. Hightower

[57] ABSTRACT

Methods are provided for making certain m-aminophenols using a sulfonation/alkali fusion procedure. The aminophenols are key intermediates in the synthesis of dyes, particularly efficient, stable dyes for laser application. Preparations of some rhodamine and phenoxazone dyes from the m-aminophenols are described.

5 Claims, No Drawings

PREPARATION OF CERTAIN M-AMINOPHENOLS AND THE USE THEREOF FOR PREPARATION OF LASER DYES

The U.S. government has rights in this invention pursuant to Contract No. W-7405-ENG-48 between the United States Department of Energy and University of California for the operation of the Lawrence Livermore National Laboratory.

BACKGROUND OF THE INVENTION

The present invention relates to methods for preparation of certain m-aminophenols which are useful to prepare dyes. In particular, the aminophenols are useful for preparing dyes having use in laser applications, printing inks, fluorescent signs and recreational equipment, fluorescent tags in diagnostic methods, as well as in other products and methods where fluorescent materials are used.

Dyes having use in laser applications are disclosed in U.S. Pat. Nos. 3,932,415, and 4,005,092, both of which in particular disclose the preparation of 8-hydroxy-2,3,6,7-tetrahydro-1H,5H-benzo[i,j]quinolizine and a method for converting it to 9-(2-carboxyphenyl)2,3,6,7,12,13,16,17-octahydro-1H,5H,11H,15H-diquinolizino-[1,9-bc;1',9'-h,i]xanthylium chloride (also known as Rhodamine 101). U.S. Pat. Nos. 4,005,092, 3,932,415 and 3,822,270 further disclose preparation of 1,2,3,4,8,9,10,11-octahydro-6-(2-carboxyphenyl)-dipyrido[3,2-b;2',3'-i]xanthylium perchlorate using 7-hydroxy-1,2,3,4-tetrahydroquinoline as a starting material. J. V. Braun, *Chem. Ber.*, 47, 492 (1914) discloses preparation of 7-hydroxy1,2,3,4-tetrahydroquinoline by a series of steps consisting of nitration of 1,2,3,4-tetrahydroquinoline to form the 7-nitro derivative, benzoylation of the amine, reduction of the nitro group to the 7-amino derivative, diazotization to the 7-phenol, and hydrolysis of the benzoyl group. Hammond and Atkins, *J. Heterocyclic Chem.*, 12, 1061 (1975), disclose the preparation of 1,2,3,4-tetrahydro-7-hydroxyquinoline by hydrogenation of 7-hydroxy-quinoline.

Sulfonation by fuming sulfuric acid to form the sulfonate followed by alkaline fusion has been described for making m-aminophenol, m-dimethylaminophenol and m-diethylaminophenol (German Pat. No. 44,792 (1888)), m-methylaminophenol and m-ethylaminophenol (German Pat. No. 48,151 (1889)), 3-methylamino-4-cresol(OH-1), 3-ethylamino-4-cresol-(OH-1) (German Pat. No. 69,074 (1892)). However, such procedures have heretofore not been applied to 1-alkyl-1,2,3,4-tetrahydroquinoline.

The above known methods for preparing 1-alkyl-1,2,3,4-tetrahydroquinolines and 7-hydroxy-1,2,3,4-tetrahydroquinolines have drawbacks for preparing aminophenols in large quantities because they are lengthy and inefficient due to a low overall yield and process complexity.

It is thus desirable to have a method for producing N-substituted-7-hydroxyquinolines which is not only simple and efficient but which also results in overall high yield of the desired product utilizing readily available and inexpensive starting materials.

SUMMARY OF THE INVENTION

Accordingly, it is an object of the present invention to provide aminophenol intermediates useful for synthesizing dyes.

It is another object of the present invention to provide dyes having laser applications which have improved efficiency and photochemical stability.

It is another object of the present invention to provide novel methods for producing improved dyes for laser applications.

These and other objects and advantages of the invention will be apparent in the description of the specific embodiments thereof, given by way of example, to enable one skilled in the art to readily practice the invention which is described hereinafter.

In general, the present invention is directed to methods for preparing 1-substituted-1,2,3,4-tetrahydro-7-hydroxyquinolines of the general Formula I:

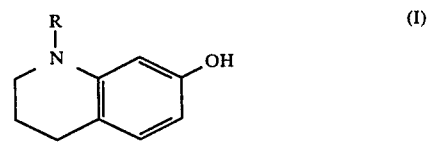

and use thereof to prepare dyes of the general Formulas II and III set forth below wherein R is hydrogen or a linear or branched alkyl of 1 to 10 carbon atoms and R' is hydrogen, a linear or branched alkyl of 1 to 10 carbon atoms, or aralkyl. Preferably, R and R' may be independently alkyl of 1 to 4 carbon atoms.

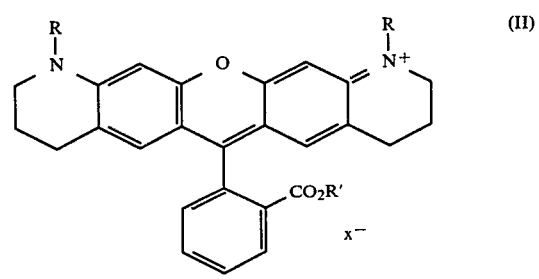

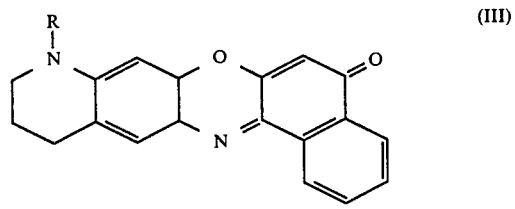

The present invention further provides novel dyes of the Formulas II C, II E below and III above, and use thereof as fluorescent dyes.

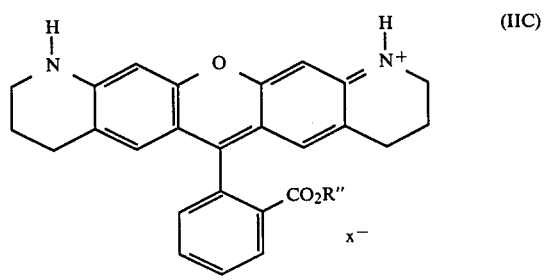

R″=linear or branched alkyl of 1 to 10 carbon atoms or aralkyl. Preferably, R″ may be alkyl of 1 to 4 carbon atoms.

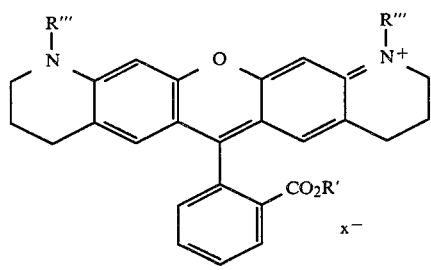

(IIE)

R' = H, linear or branched alkyl of 1 to 10 carbon atoms or aralkyl. Preferably, R' may be alkyl of 1 to 4 carbon atoms.

R''' = linear or branched alkyl of 1 to 10 carbon atoms, preferably alkyl of 1 to 4 carbon atoms.

The invention is further directed to improved methods for making rhodamine dyes by phosphoric acid condensation of intermediates of the Forumlas IB and IC:

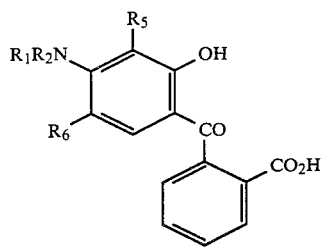
(IB)

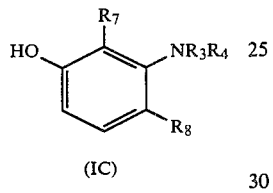
(IC)

wherein $R_1$, $R_2$, $R_3$, $R_4$, $R_5$, $R_6$, $R_7$, and $R_8$ are independently selected from hydrogen or linear or branched alkyl containing 1 to 10 carbon atoms, and $R_1$–$R_5$, $R_2$–$R_6$, $R_3$–$R_7$ and $R_4$ and $R_4$–$R_8$ may independently form portions of a nitrogen-containing 5 or 6-membered alicyclic ring. Alkyl groups of 1 to 4 carbon atoms are preferred.

The carboxyl group of the resultant condensation product of IB and IC may be esterified by a conventional esterification agent. Preferred esters are the methyl, ethyl, n-propyl and n-butyl esters.

DETAILED DESCRIPTION OF THE INVENTION

These and other objects of the invention are accomplished by providing a class of 1-substituted-1,2,3,4-tetrahydro-7-hydroxyquinoline intermediates of the Formula (I):

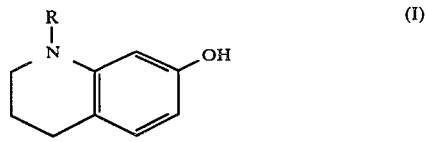
(I)

wherein R is hydrogen or linear or branched alkyl of 1 to 10 carbon atoms. Preferably, R may be alkyl of 1 to 4 carbon atoms. The method for providing (I) comprises the steps of treating a 1-substituted-1,2,3,4-tetrahydroquinoline of the Formula (IA):

(IA)

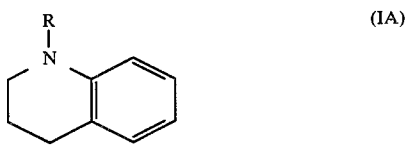
(IA)

with a sulfonating agent to form a 7-sulfonated derivative of IA; and fusing the product of the first step with alkaline metal hydroxide. Sulfonating agents usually employed include oleum (a solution of sulfur trioxide in concentrated sulfuric acid, also known as fuming sulfuric acid) and acid sulfates. Alkaline metal hydroxides utilized for the fusion step include but are not limited to sodium hydroxide, potassium hydroxide, lithium hydroxide and mixtures thereof. A mixture of sodium hydroxide and potassium hydroxide is the preferred agent.

Compound IA may be prepared by initially N-alkylating quinoline and hydrogenating N-alkyl quinolinium salt. Typical alkylating agents include but are not limited to dimethyl sulfate, diethyl sulfate, methyl hydrogen sulfate, aliphatic halides, and the like.

A preferred embodiment for making compounds of the Formula I (where R is not hydrogen) is set forth below in Scheme 1:

Scheme 1

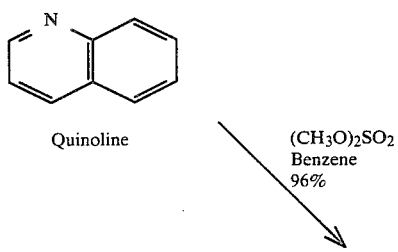

Quinoline     $(CH_3O)_2SO_2$
Benzene
96%

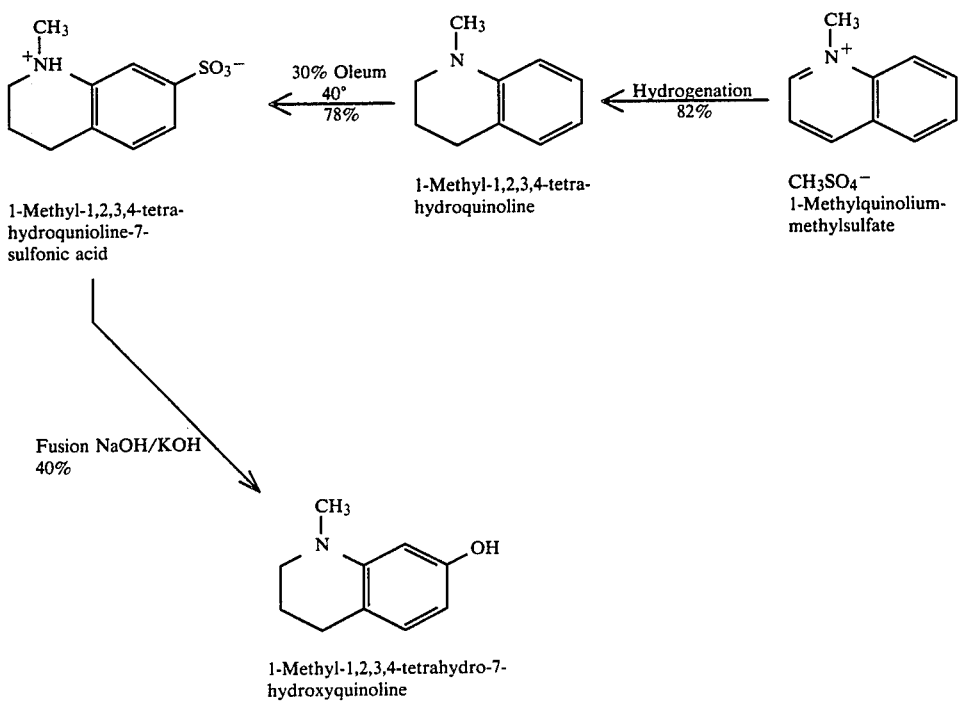

Scheme 1 is shown for the preparation of compounds of the Formula I wherein R is methyl, however, it is readily apparent that other N-alkyl homologs or analogs may be made using appropriate alkylating agents. As shown in Scheme 1, the inexpensive and plentiful base quinoline found in coal-tar is N-alkylated by an alkylating agent, such as dimethylsulfate. This step appears to be quantitative and precipitates the quaternary quinolium salt. Although deliquescent, the salt is sufficiently wetted by the aromatic solvent benzene to permit handling. The quinolinium salt may then be reduced by known methods, for example, using tin and hydrochloric acid (A. Feer and W. Koenigs, Chem. Ber., 18, 2388 (1885); J. Meisenheimer, Justus Liebigs. Ann. Chem., 385, 117 (1911)); or by catalytic hydrogenation with Raney nickel (J. Barltrop and D. Taylor, J. Chem. Soc., 108 (1951)) or platinum (German Pat. No. 750,399 (1945); C. Bahner, W. Easley and E. Stephen, J. Amer. Chem. Soc., 74, 4198 (1952); S. Hünig and K. Requardt, Justus Liebigs. Ann. Chem., 592, 180 (1955)); anhydrous formic acid and triethylamine (A. Kost and L. Yudin, J. Gen. Chem. USSR (Eng.), 26, 1929 (1956)); or in a one step process from quinoline with sodium borohydride, and an aliphatic acid such as formic acid (G. Gribble and P. Heald, Synthesis, 650 (1975)). Catalytic hydrogenation with Adams catalyst is described below, where the catalyst may be filtered and reused at the end of each reaction. The resulting 1-alkyl-1,2,3,4-tetrahydroquinoline may be purified by fractional distillation, crystallization or by other conventional methods.

The sulfonation of 1-methyl-1,2,3,4-tetrahydroquinoline (IA,R=methyl), or of 1,2,3,4-tetrahydroquinoline (IA,R=H), is achieved by slowly dropping the compound into stirred 30% fuming sulfuric acid (SO$_3$ in concentrated sulfuric acid) at a rate such that there is no rapid increase in temperature. A reaction temperature of about 40° C. is suitable. The 7-monosulfonate which is formed exclusively in high yield may be isolated as the free acid from aqueous solution or may be salted out from aqueous solution by saturation with an inorganic salt, such as sodium chloride. Other salts such as potassium chloride may be employed. Sulfonation exclusively at the 7 position may be confirmed by $^{13}$C nmr and by X-ray diffraction analysis of the crystalline sulfonates.

The final step shown in Scheme 1 is an alkali fusion. The 7-sulfonated derivatives are first converted into corresponding sodium salts by dehydration under vacuum, preferably at 1 mm of Hg at elevated temperatures of around 120° C. for about 2 hours. Sodium hydroxide and potassium hydroxide are preferably used in combination since such a system can have a lower melting point than either component alone.

The above-described general method may also be utilized to prepare another useful dye intermediate, 1,2,3,4-tetrahydro-7-hydroxyquinoline (I,R=H). Prior art methods of making this compound have been lengthy and expensive, i.e., the method of J. V. Braun, supra, or the method of P. Hammond and R. Atkins, J. Heterocyclic Chem., 12, 1061 (1975), utilizing hydrogenation of the expensive 7-hydroxyquinoline. Thus, 1,2,3,4-tetrahydroquinoline (IA,R=H) may be sulfonated and fused with alkali as shown below in Scheme 2 to produce 1,2,3,4-tetrahydro-7-hydroxyquinoline.

Scheme 2

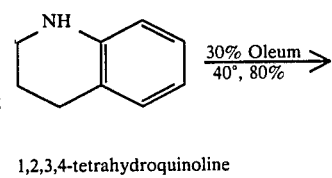

1,2,3,4-tetrahydroquinoline

-continued
Scheme 2

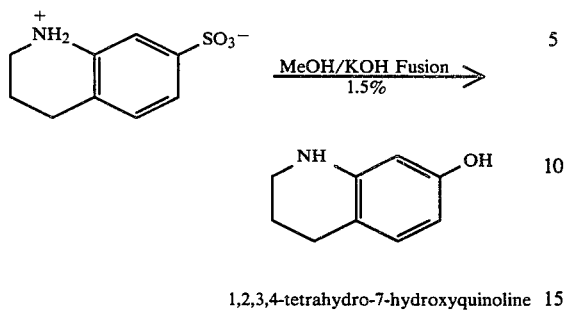

1,2,3,4-tetrahydro-7-hydroxyquinoline

The aminophenol intermediates of the Formula I may be utilized to prepare improved dyes for laser applications, particularly dyes of the rhodamine and phenoxazone classes.

The compounds according to Formula (I) may be converted to improved rhodamine class of laser dyes of the Formulas (II) and (III):

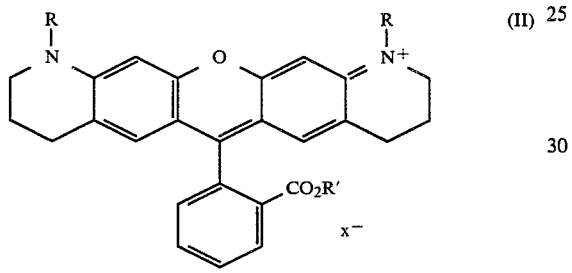

-continued 1,11-disubstituted-1,2,3,4,8,9,10,11-octahydro-6-(2-carboxyphenyl)-dipyrido[3,2-b:2′,3′-i]xanthylium salt (III)

9,10,11,12-tetrahydro-9-subsitiuted-5H—benzo-[α]pyrido[2,3-i]phenoxazin-5-one.

wherein R and R' are as previously described and X⁻ is an anion of a salt, preferably inorganic, such as a halide, sulfate, perchlorate, fluoroborate, borate, phosphate and the like. Chloride, perchlorate and fluoroborate salts are preferred for ease of preparation, use and convenience.

Compounds of the Formula (II) may be further alkylated to form esters which have improved properties as laser dyes. Additionally, the aminophenol intermediates according to the present invention may be used to prepare other efficient, stable laser dyes whose chromophores terminate in a free amino radical, including such dyes as the rhodamines, pyronins, oxazines, 7-aminocoumarins, chromogens and oxazones.

Generally, 1-alkyl-1,2,3,4-tetrahydro-7-hydroxyquinolines (I) may be converted into useful laser dyes (2a) and (2b) as shown below in Scheme 3.

Scheme 3

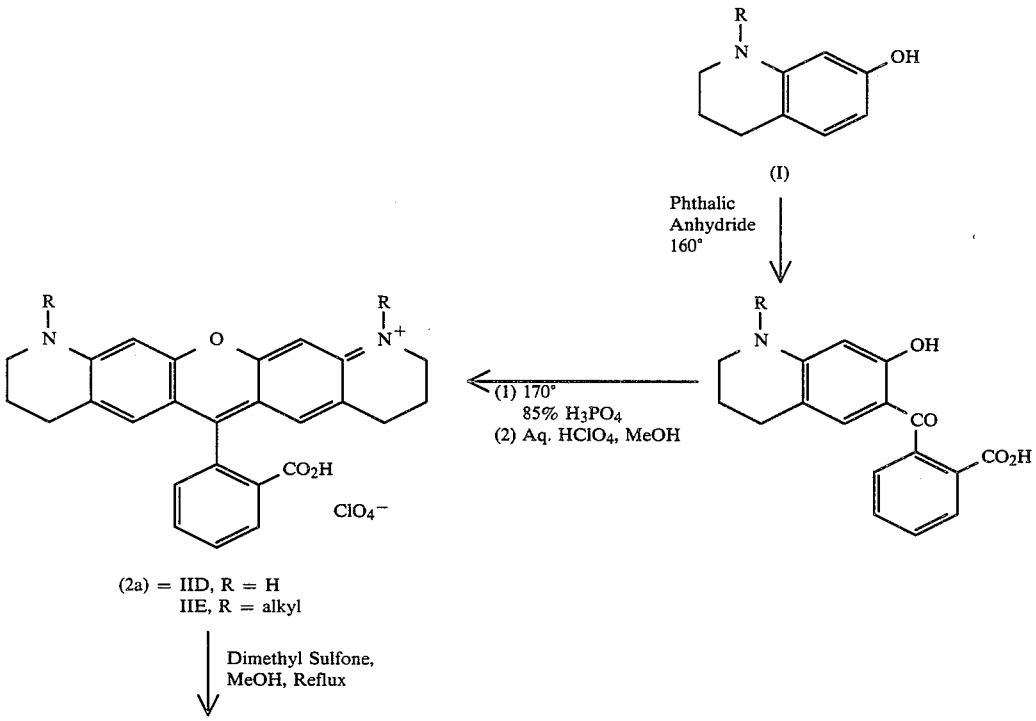

(2a) = IID, R = H
IIE, R = alkyl

-continued
Scheme 3

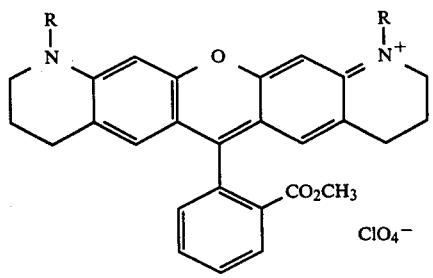

(2b) = IIC, R = H
IIE, R = alkyl

As indicated in Scheme 3, two equivalents of the aminophenol (I) are condensed with phthalic anhydride. The second equivalent is condensed in the presence of an acid catalyst. Strong, non-oxidizing, dehydrating acids are suitable as the acid catalysts. Exemplary acids include phosphoric acid, boric acid, substituted phosphonic acids, and substituted sulfonic acids. The acid of choice is 80-90% phosphoric acid, preferably the azeotrope, 85% phosphoric acid. Although sulfuric acid may be employed, the ring-constrained aminophenol is readily oxidized by sulfuric acid, thereby reducing the overall yield of the dye product significantly. Unexpectedly superior yields are obtained when 85% phosphoric acid is used as the acid catalyst.

Esterification of the rhodamine (2a in Scheme 3) carboxyl group may be achieved by known techniques. The preferred esters are the methyl, ethyl, n-propyl and n-butyl esters. Also, esterification may be done by refluxing the dye in anhydrous methanol/dimethyl sulfate or anhydrous ethanol/diethyl sulfate solution to form the ester (2b) until reaction is complete. The ester (2b) may be crystallized from the hot solution by adding warm water and cooling. Alternatively, the carboxyl dye (2a) may be esterified by refluxing in anhydrous alcohol in the presence of the acid form of an ion exchange resin, such as Amberlite IR-120 until completely reacted. The filtered solution will contain substantially pure dye.

The 1-alkyl-1,2,3,4-tetrahydro-7-hydroxyquinoline compounds according to the present invention may also be utilized to synthesize dyes of the phenoxazone class represented by Formula (III). The compound (I) may be nitrosylated by known methods to form 1-alkyl-1,2,3,4-tetrahydro-6-nitroso-7-hydroxyquinoline. Exemplary nitrosylating agents include nitrous acid, sodium nitrite, potassium nitrite, magnesium nitrite, lithium nitrite, and the like. Sodium nitrite is preferred. This may be then condensed with 1,3-dihydroxynaphthalene to produce compounds of Formula (III). This method is an improvement over the method of Mohlau and Uhlmann, *Justus Liebigs. Ann. Chem.*, 289, 90 (1896), which discloses the condensation of 2-nitroso-5-dialkylaminophenols with 1-naphthol. According to the present invention, improved yields of the product are obtained based on the consumption of the nitrosoalkylaminophenol.

It has also been found that phosphoric acid catalyzed condensation is an efficient method for making dyes of the rhodamine class having the Formula IV:

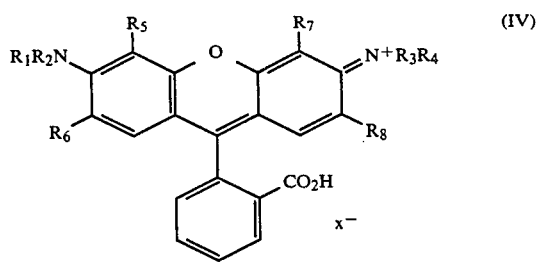

wherein $X^-$ is an anion, such as, for example, chloride, fluoroborate, perchlorate and the like, and $R_1$, $R_2$, $R_3$, $R_4$, $R_5$, $R_6$, $R_7$, $R_8$ are independently selected from H or linear or branched alkyl containing from 1 to 10 carbon atoms, and wherein $R_1$–$R_5$, $R_2$–$R_6$, $R_3$–$R_7$ and $R_4$–$R_8$ may independently each form portions of a nitrogen containing 5 membered or 6 membered alicyclic ring. Preferably, $R_1$, $R_2$, $R_3$, $R_4$, $R_5$, $R_6$ and $R_7$ are independently alkyl of 1 to 4 carbon atoms. Esterification of (IV) may be accomplished as discussed above in the preparation of (2b) from (2a). The methyl, ethyl, n-propyl and n-butyl esters of IV are preferred.

Dyes of the Formula (IV) and open ring homologs and analogs thereof may be made by phosphoric acid catalyzed condensation of compounds of the Formula IB and IC:

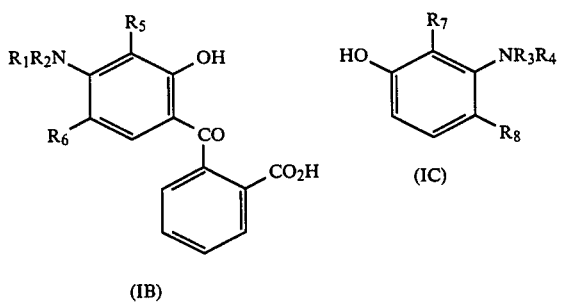

wherein $R_1$, $R_2$, $R_3$, $R_4$, $R_5$, $R_6$, $R_7$, and $R_8$ are described above. The carboxyl group of the resultant condensation product of IB and IC may be esterified by known techniques. The methyl, ethyl, n-propyl and n-butyl esters are preferred.

Compound IB may be obtained by condensation of one equivalent of the phenol ID:

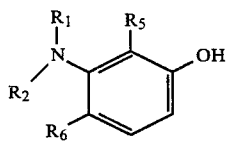

with phthalic anhydride. Also, the phenol (ID) may be identical to or different from phenol (IC). Compounds (IC) and (ID) may be identical to or different from compound (I). Compounds IC and ID may be obtained from m-aminophenols of the Formula I or derivatives thereof by ring cleavage and/or substitution at appropriate ring positions. For example, compounds IC and ID may be selected from the following heterocycles:

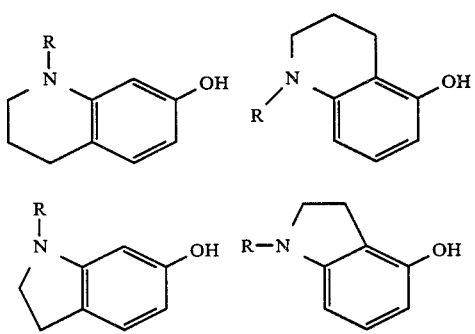

and may be prepared by ring cleavage of the alicyclic ring and by substitutions at the appropriate positions on the rings. The methods for ring opening and ring substitutions are known to those skilled in the art.

The dyes made in accordance with the present invention show improved efficiency and lower excitation threshold for laser action as well as improved photochemical stability. The dyes made according to the present invention are improvements in the laser dye art due to their improved longevity. This is particularly advantageous in systems which are designed for continuous operation utilizing laser dyes.

The fluorescent dyes prepared in accordance with the methods of the subject invention are also useful in the preparation of printing inks, fluorescent posters, road safety signs, fluorescent toys, and other products where fluorescent dyes are used, and in chemical and biological research, in therapeutic and diagnostic kits and pharmaceutical products where fluorescent markers or tags are desired or employed.

The following examples are presented to help in the better understanding of the subject invention and for purposes of illustration only. They are not to be constructed as limiting it to the precise form disclosed or to limit the scope of the invention in any manner or means.

EXAMPLE 1

Preparation of N-methylquinolinium methylsulfate.

Pure, commercial grades of quinoline, benzene and dimethylsulfate were stored over Molecular Sieve 4A for two days prior to reaction. Into a three liter, three-necked round bottomed flask fitted with an electrical heater, stirrer, dropping funnel and an efficient reflux condenser equipped with calcium chloride drying tube were placed quinoline 300 ml. (328.8 g., 2.54 moles) in benzene 900 ml. Dimethyl sulfate 240 ml. (319.2 g., 2.53 moles) in benzene 180 ml. was run in rapidly over five minutes while the contents were vigorously stirred. Spontaneous warming and refluxing occurred and the liquid separated into two phases. After the initial reaction had subsided the flask was heated to reflux for two hours and then allowed to cool for two hours. All the time the reagents were vigorously stirred until the cooled mixture became a suspension of small particles. These were filtered as far as removing Cthe solvent, washed with benzene 1000 ml. and refiltered, and were transferred to tared bottles in a vacuum desiccator over sulfuric acid and sodium hydroxide. The desiccator was evacuated at room temperature for about six hours when no further benzene was collected in a liquid nitrogen trap. Total yield of dried material 633.5 g. (98%).

EXAMPLE 2

Preparation of 1-methyl-1,2,3,4-tetrahydroquinoline (kairoline M)(IA,R=methyl)

N-Methylquinolinium methosulfate 450 g. and platinum oxide 5.0 g. in methanol 1.2 l. were agitated and warmed to 45° in a Parr 2 l. hydrogenator. Hydrogen uptake was theoretical and complete in two and a half hours. The solution was filtered and evaporated to dryness, and the catalyst reused. The amber gum was dissolved in dichloromethane 800 ml., which was washed with 10% aqueous sodium hydroxide 800 ml., water 800 ml., and was dried over sodium sulfate. Evaporation of the solvent left a light brown mobile oil 260 g. Several hydrogenation fractions were combined 830 g. and distilled, and the fraction boiling between 75° and 79° at 1 mm. collected as kairoline 762 g. (92%).

EXAMPLE 3

Preparation of 1-methyl-1,2,3,4-tetrahydroquinoline-7-sulfonic acid

30% Oleum (fuming sulfuric acid) 120 ml. was contained in a 500 ml. fournecked round-bottomed flask equipped with thermometer, short reflux condenser with drying tube, stirrer and a precision dropping funnel. The whole was surrounded with an ice-water jacket. Kairoline (Example 2) 45 ml. (45.9 g.) was dropped slowly over about half an hour into the rapidly stirred oleum so that the temperature did not exceed 40° and the mixture was warmed in a 55° water-bath for another hour. The oil was poured onto ice 270 g., and the pale yellow solution was cooled, mixed with acetone 1 l. and stored at −30° overnight. The flask was swirled to dislodge the crystals and to fully seed the solution and was stored at −30° a further three hours. Filtration, two washings with acetone and drying in the laboratory atmosphere gave 53.2 g. (75%) of white crystals.

The material recrystallized from water had mp. 306° C. (dec.).

Analysis calculated for $C_{10}H_{13}NO_3S$: C, 52.9; H, 5.7; N, 6.2; S, 14.1. Found: C, 53.1; H, 5.8; N, 6.2; S, 14.1.

EXAMPLE 4

Extraction of 1-methyl-1,2,3,4-tetrahydroquinoline 7-sulfonic acid as the sodium salt A reaction mixture as obtained from the above oleum sulfonation was slowly dripped over half an hour into a stirred, saturated aqueous solution of sodium hydroxide 204 g. and sodium chloride 348 g. in water—total volume 1.6 l., and was stirred and allowed to cool another half hour. Filtration and drying gave 154 g. of a mixture of sodium sulfonate and sodium sulfate, which was extracted with boiling alcohol 1.5 plus 0.2 l. The filtered solution was cooled at 0° overnight, filtered through a large Buchner funnel using Whatman 4 filter paper and dried in the atmosphere to give 51.4 g. (62%) of pale yellow crystalline plates.

Recrystallized from alcohol and dried at 60° at 0.1 mm for two hours it had mp. 314° (dec.).

Analysis calculated for $C_{10}H_{12}NO_3Sna.H_2O$: C, 45.0; H, 5.2; N, 5.2; S, 12.0. Found: C, 45.0; H, 5.3; N, 5.3; S, 11.9.

EXAMPLE 5

Conversion of 1-methyl-1,2,3,4-tetrahydroquinoline-7-sulfonic acid to the sodium salt The kairoline-7-sulfonate 22.7 g. and sodium hydroxide 4.0 g. were stirred and brought to reflux in 200 ml. alcohol for five minutes and were cooled at 0° overnight. Filtration and drying gave 23.2 g. (85%) of the sodium salt. Alternatively, evaporation to dryness of the reaction mixture gave 26.7 g. (100%), which on heating at 120° at 1 mm. for two hours diminished to 24.9 g. (the anhydrous salt).

EXAMPLE 6

Preparation of 1,2,3,4-tetrahydroquinoline-7-sulfonic acid

Into 200 ml. of 30% oleum contained in a 1 l. flask equipped as for the kairoline sulfonation, was dripped 75 ml. (79.5 g.) of 1,2,3,4-tetrahydroquinoline. The reaction vessel was cooled in ice-water and the rate was controlled to maintain a temperature of 40°, the total addition requiring 50 minutes. The mixture was warmed to 50° for two hours, it was then slowly dripped into stirred water 1.25 l. and the solution was left to cool for two hours. The precipitated material was filtered, washed with 500 ml. of ice-cold water and dried in the atmosphere to give 116 g. (84%).

It crystalled from water as pale cream crystals, mp. greater than 316° (dec.).

Analysis for material dried at room temperature, 0.1 mm. for two hours, calculated for $C_9H_{11}NO_3S.H_2O$: C, 46.8; H, 5.6; N, 6.1; S, 13.8. Found: C, 46.9; H, 5.6; N, 6.0; S, 14.1; and for material dried at 60°, 0.1 mm. for two hours, calculated for $C_9H_{11}NO_3S$: C, 50.7; H, 5.2; N, 6.6; S, 15.1. Found: C, 50.5; H, 5.2; N, 6.5; S, 15.0.

EXAMPLE 7

Conversion of 1,2,3,4-tetrahydroquinoline-7-sulfonic acid to the sodium salt

The sulfonic acid 23.1 g., sodium hydroxide 4.0 g. and bumping stone in methanol 100 ml. were refluxed for five minutes, cooled and evaporated to dryness to give 25.3 g. which on heating at 120° at 1 mm. for two hours diminished to 23.4 g.

EXAMPLE 8

Alkali fusion of sodium 1-methyl-1,2,3,4-tetrahydro-quinoline-7-sulfonate

For most experiments fusion mixtures were contained in a crucible covered by a borosilicate clock-glass and were heated in a silicone 710 oil bath. Holes in the clock-glass permitted entry of an efficient stirrer, and a tube introducing a stream of nitrogen together with a chromel-alumel thermocouple.

The bath temperature was brought to 260° and a mixture of sodium hydroxide 60 g. and potassium hydroxide 40 g. was allowed to fuse. The anhydrous sodium sulfonate 20 g. was added in portions and each was well stirred and wetted by the liquid alkali before the next addition. The light brown sludge slowly darkened, generally producing a spongy cap to the reaction mixture which had to be broken and pushed into the stirred melt. After six hours, all solid had disappeared to produce a dark liquid and brown liquid drops were present on the undersurface of the clock-glass. This was poured directly into water 500 ml. in a conical flask and the the crucible was washed with another 100 ml. of water. The solution was cooled and extracted with benzene 50 ml., and the benzene extract after drying and evaporation gave 0.4 g. of brown oil consisting mainly of kairoline. The alkali solution was made acid pH 1 to 2 with 190 ml. of concentrated hydrochloric acid, sulfur dioxide could be smelt, and the cooled liquid was filtered. Powdered sodium carbonate (about 10 g.) was added to the stirred solution until the pH reached 8 when a light brown gummy precipitate appeared. This was extracted into benzene 150 ml. plus 100 ml., the benzene extract washed with water, dried ($Na_2SO_4$) and evaporated to give a clear brown gum which crystallized on standing 52 g. (40%). If chloroform was used for the extraction process emulsions developed which had to be separated by centrifuging.

The material was frequently obtained as a brown viscous gum, particularly if it had been extracted as a chloroform solution, and was useable directly for dye synthesis. It could be crystallized from a small volume of benzene to give 1-methyl-1,2,3,4-tetrahydro-7-hydroxyquinoline as a colorless solid, mp. 97°-98°, which slowly darkened on standing.

Analysis calculated for $C_{10}H_{13}NO$: C, 73.6; H, 8.0; N, 8.6. Found: C, 73.5; H, 8.1; N, 8.6.

A more efficient purification was low pressure distillation in a nitrogen atmosphere where it was collected at 150° at 1.1 mm. The equipment used had a small, lagged Claisen head, and a five inch air condenser that ran directly to the collection flask without ground-glass connections. The reason for this is that the product came over as a viscous oil, which readily crystallized, and which frequently had to be warmed for transfer to the receiver.

EXAMPLE 9

Alkali fusion of sodium 1,2,3,4-tetrahydroquinoline-7-sulfonate

Potassium hydroxide 69 g. and sodium hydroxide 100 g. were fused at 235°. The anhydrous sodium sulfonate 21.4 g. was added in portions and stirred into the melt over twenty minutes. The mixture frothed and within an hour was becoming darker and more liquid. Even after four hours though there was still suspended solid. The melt was poured into water 700 ml., which was acidified with 316 ml. of concentrated hydrochloric acid, cooled and filtered. Neutralization with sodium carbonate (pH 8) gave a brown oil, which was extracted with benzene 200 plus 100 ml. The benzene was washed with water, dried and evaporated to give 5.7 g. of a dark gum that solidified. This was stirred in 10% aqueous sodium hydroxide, filtered from insoluble material and extracted with benzene. The benzene extract contained 1.9 g. of oil identified as mainly 1,2,3,4-tetrahydroquinoline and quinoline. The sodium hydroxide solution was acidified, neutralized with sodium carbonate, extracted with benzene and the benzene layer was dried and evaporated to give 0.2 g. of 1,2,3,4-tetrahydro-7-hydroxyquinoline.

crystalline solid that slowly darkens under ambient laboratory conditions over several weeks.

TABLE 1

| | | | Alkali fusion experiments | | | | | |
|---|---|---|---|---|---|---|---|---|
| | | Mole fraction composition (%) | | | Temp. | Time | Yield | |
| Run | Sulfonate* | | NaOH | KOH | Water | (°C.) | (Hrs) | (%) | Comments |
| 1 | A | 3 | 57 | 24 | 16 | 300 | 2 | 6 | |
| 2 | A | 3 | 57 | 24 | 16 | 290 | 2.5 | 40 | |
| 3 | A | 3 | 57 | 24 | 16 | 280 | 23 | 41 | |
| 4 | A | 2 | 40 | 16 | 41 | 290 | 16 | 18 | |
| 5 | A | 2 | 40 | 16 | 41 | 280 | 5 | 21 | Clean product |
| 6 | A | 3 | 57 | 24 | 16 | 260 | 6 | 40 | Clean product |
| 7 | A | 3 | 48 | 48 | 0 | 225 | 7 | 10 | Impure product, plus kairoline (10%) |
| 8 | A | 2 | 38 | 38 | 22 | 240 | 20 | 26 | Clean product |
| 9 | B | 3 | 58 | 24 | 16 | 265 | 5 | 0 | |
| 10 | B | 2 | 58 | 24 | 16 | 235 | 4 | 1.3 | Multiple products |
| 11 | B | 3 | 48 | 48 | 0 | 200 | 1.5 | 0 | Multiple products, including Tetrahydroquinoline |

*A 7-Sodium sulfonate of 1-methyl-1,2,3,4-tetrahydroquinoline
B 7-Sodium sulfonate of 1,2,3,4-tetrahydroquinoline

EXAMPLE 10

Conditions of Alkali Fusion

The results of a number of alkali fusions, following the procedure of Example 8, are shown in Table 1. The sulfonates were converted into the sodium salts which in each case were dehydrated from their single molecule of water of crystallization by prior heating in a vacuum oven (1 mm of mercury, 120° C.) for two hours. Fresh commercial sodium hydroxide (2% by weight water) and potassium hydroxide (15% by weight water) were used in combination, the mixed systems having a lower melting point than either component (H. Otto and R. Seward, J. Chem. Eng. Data, 9, 507 (1964)). At the temperature of reaction (maximum 300°) the water compositions of the melt were assumed to be the same as prepared at room temperature. For complete dehydration the alkali mixture was heated to 500° for two hours prior to reaction. All fusions were conducted under a stream of nitrogen.

Completely dehydrated alkali appears to be a vigorous reagent attacking the sulfonates even at low temperature to give multiple products including the free bases (kairoline or tetrahydroquinoline), as shown by runs 7 and 11. Presence of water moderates the reactivity, as shown by comparing runs 2 and 4, 3 and 5. However, in run 8 there is no reaction with kairoline sulfonate at temperatures below 240°. Even for an alkali mixture which has not been prefused at 500°, a reaction temperature greater than 290° results in loss of product, as shown by comparing runs 1 and 2. Highest yields of 1-methyl-1,2,3,4-tetrahydro-7-hydroxyquinoline in a form that promptly crystallizes on standing, having a clean nmr spectrum and suitable for dye synthesis, are obtained with alkalis direct from the bottle, reacting at lower temperature (260°) and longer time (6 hrs). An intermediate step in the work-up is to neutralize an acid aqueous solution with sodium carbonate where the product is precipitated and may be filtered off. Organic solvent extraction may be used and benzene, rather than chloroform which produces emulsions, is a preferred solvent. The aminophenol may be purified by crystallization from a small volume of benzene or, preferably, by vacuum distillation where it is obtained as a colorless

EXAMPLE 11

Preparation of 1,11-dimethyl-1,2,3,4,8,9,10,11-octahydro-6-(2-carboxyphenyl)-dipyrido[3,2-b:2'3'-i]xanthylium perchlorate

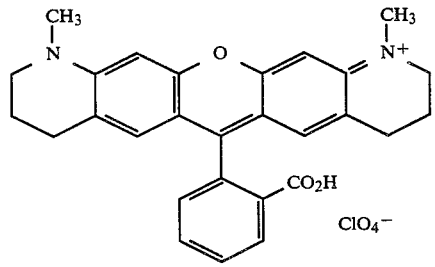

(IIE, R''' = CH$_3$, R' = H)

1-Methyl-1,2.3,4-tetrahydro-7-hydroxyquinoline 10.0 g. (0.061 mole) and phthalic anhydride 14.0 g. (0.094 mole) were heated in a 1 l. rb flask fitted with reflux condenser in an oil bath at 160° for three hours. The initial melt was mobile and was thoroughly mixed by hand-rotating the flask, and slowly became viscous. To the cooled mixture were added 1-methyl-1,2,3,4-tetrahydro-7-hydroxyquinoline 10.0 g. and 24 ml. of 85% phosphoric acid. The contents were heated under reflux in an oil-bath at 170° for three hours, and the flask was intermittently agitated for the first fifteen minutes to ensure even dispersal. To the still warm mixture were added a methanol solution of perchloric acid (24 ml. of 50% aqueous perchloric acid in 360 ml. of methanol), and the flask was refluxed. Within ten minutes, copious crystals of the rhodamine perchlorate appeared. The flask was stored overnight at 0°, and filtration gave 24.0 g. (73%) of golden metallic crystals.

The material recrystallized from methanol/water (1:1 v/v) had mp. 260°–265° (dec.).

Analysis calculated for C$_{28}$H$_{27}$N$_2$ClO$_7$: C, 62.4, H, 5.1; N, 5.2. Found: C, 62.1; H, 5.3; N, 5.0.

EXAMPLE 12

Preparation of 1,11-dimethyl-1,2,3,4,8,9,10,11-octahydro-6-(2-methoxy carbonylphenyl)-dipyrido[3,2-b:2'3'-i]xanthylium perchlorate

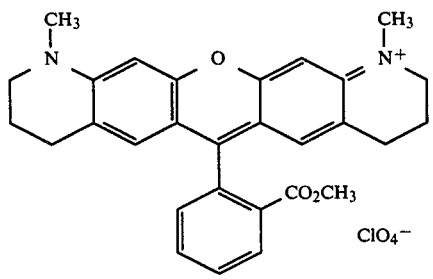

(R''' = CH$_3$, R' = CH$_3$)

The dye prepared as described in Example 11, dried at 1 mm., 60° for 2.5 hours, 69.5 g. was stirred and refluxed in an anhydrous methanol solution of dimethyl sulfate (25.0 ml. in 800 ml.) for 72 hours. The reflux condenser was protected with a calcium chloride drying tube. Chromatography on thin-layer alumina, using i-propanol eluant, indicated almost complete conversion to the ester. Warm water (65°, 800 ml.) was carefully and evenly added, the solution refluxed and rapidly filtered through No. 4 paper, and was left at 0° overnight. The dark green crystals were filtered and washed with a small volume of cold methanol/water (1:1 v/v). Total yield was 53.2 g. of air-dried material, together with a second small crop from the mother liquor 1.1 g. (77%), pure according to thin layer chromatography.

The compound recrystallized from methanol/water (1:1 v/v) had mp. 212°-214° (dec. 239°).

Analysis calculated for C$_{29}$H$_{29}$N$_2$ClO$_7$: C, 63.0; H, 5.3; N, 5.1; Cl, 6.4. Found: C, 62.8; H, 5.5; N, 5.1; Cl, 6.5.

This rhodamine class dye has an absorption maximum at 559 nm and a fluorescence maximum at 583 nm in ethanol. It has high fluorescence quantum yields (approximately 99%) in a number of solvents—alcohols (methanol, ethanol, propanol, benzyl alcohol, trifluoroethanol), dimethyl sulfoxide and acetonitrile. It shows improvement in laser performance and stability compared with other dyes that operate in the same wavelength region, such as, rhodamine B and kiton red S.

EXAMPLE 13

Comparison of Dye of Example 12 with kiton red S dye

Two 10$^{-4}$ molar solutions in methanol/water (50% v/v) of the dye prepared in Example 12 and of kiton red S were compared in a flashlamp-pumped oscillator. The solution flowed through a 3 mm diameter, 11 cm long capillary in a cavity containing a birefringent tuning element, and was excited at 10 Hz and 14 J/pulse. Although kiton red S would not lase under these conditions, the dye, according to Example 12, showed an output at 638 nm of 5 mj/pulse, which was as strong as rhodamine 6G operating at its peak wavelength. The dye according to Example 12 can be pumped by either 510.6 nm or 578.2 nm lines of the pulsed copper vapor laser, permitting flexibility of system design, as well as by the 532 nm line of the doubled neodymium laser.

EXAMPLE 14

Preparation of 1,2,3,4,8,9,10,11-octahydro-6-(2-carboxylphenyl)-dipyrido[3,2-b:2',3'-i]xanthylium perchlorate

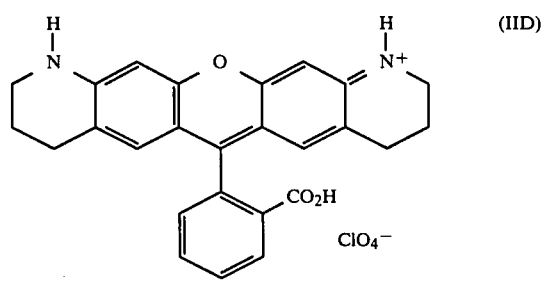

1,2,3,4-tetrahydro-7-hydroxyquinoline 3.0 g. and phthalic anhydride 3.0 g. were heated as described in Example 11. Another 3.0 g. of the amino-phenol and 85% phosphoric acid 8 ml. were added and the contents heated under reflux in an oil-bath at 170° for three hours. A solution of 50% aqueous perchloric acid 8 ml. in methanol 80 ml. was added to the cooled reaction, the mixture refluxed and cooled at 0° overnight. Filtration gave 5.0 g. (44%) of dark red crystals.

The material was recrystallized from a large volume of methanol and was found to char without melting at 333°.

Analysis calculated for C$_{26}$H$_{23}$N$_2$ClO$_7$: C, 61.1; H, 4.5; N, 5.5. Found: C, 60.8; H, 4.7; N, 5.4.

EXAMPLE 15

Preparation of 1,2,3,4,8,9,10,11-octahydro-6-(2-methoxycarbonylphenyl) dipyrido[3,2-b:2',3'-i]xanthylium perchlorate

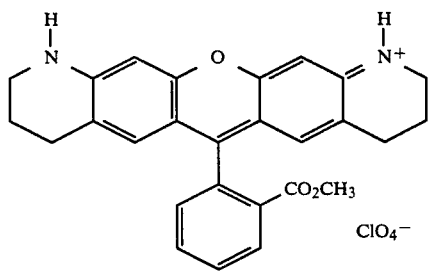

(IIC, R'' = CH$_3$)

The dye prepared as described in Example 14, 4.2 g., freshly prepared acid form of ion-exchange resin Amberlite IR 120 4.2 g. and anhydrous methanol 200 ml. were stirred and heated under reflux protected from the atmosphere by a drying tube for fifty hours. Thin layer chromatography, using i-propanol as an eluant, indicated only the ester in solution. The liquid was filtered, the resin extracted with 200 ml. of boiling methanol and the combined extracts were evaporated to dryness to give 2.2 g. (51%), pure according to thin layer chromatography.

The compound recrystallized from a large volume of methanol as dark red needles and had mp. 278° (dec.).

Analysis calculated for C$_{27}$H$_{25}$N$_2$ClO$_7$: C, 61.8; H, 4.8; N, 5.3. Found: C, 61.5; H, 5.0; N, 5.3.

EXAMPLE 16

Preparation of 9,10,11,12-tetrahydro-9-methyl-5H-benzo[a]pyrido[2,3-i]phenoxazin-5-one

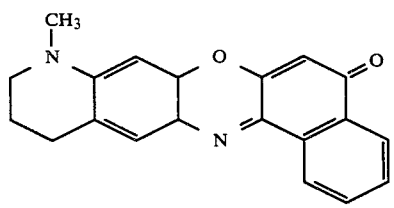

(III, R = CH₃)

1-Methyl-1,2,3,4-tetrahydro-7-hydroxyquinoline 15 g. (0.093 mole) was dissolved in a mixture of methanol 105 ml., water 70 ml., and concentrated hydrochloric acid 35 ml. and was filtered into a 500 ml. conical flask. The solution was well cooled to maintain a temperature between 0° and 5° and was rapidly stirred whilst a 10% aqueous solution of sodium nitrite 67 ml. (5% excess) mixed with methanol 67 ml. was slowly dripped in over half an hour and then stirred for another hour. The precipitate was filtered, washed with cold, dilute hydrochloric acid and air-dried to give 11.7 g. (56%) of yellow-brown fine crystals of 1-methyl-1,2,3,4-tetrahydro-6-nitroso-7-hydroxyquinoline hydrochloride.

Recrystallized from dilute hydrochloric acid it had mp. 197° (dec.).

Analysis calculated for C$_{10}$H$_{13}$ClN$_2$O$_2$: C, 52.5; H, 5.7; N, 12.2. Found: C, 52.4; H, 5.8; N, 12.2.

1,3-Dihydroxynaphthalene 18.6 g. (14% excess) was stirred and refluxed in glacial acetic acid 100 ml. and 1-methyl-1,2,3,4-tetrahydro-6-nitroso-7-hydroxyquinoline hydrochloride 23.3 g. (0.10 mole) was added in portions over half an hour. The mixture was refluxed a further one and a half hours when it became a deep ink blue. It was left to cool and settle overnight and the precipitated solid was filtered, washed twice with water, once with dilute ammonia and once with water and stored in a vacuum oven (10 mm., 60°) overnight. The solid was recrystallized from 850 ml. of pyridine to give 17.5 g. (55%) of dark green lustrous crystals.

9,10,11,12-Tetrahydro-9-methyl-5H-benzo[a]pyrido[2,3-i]phenoxazin-5-one had mp. 265°–267° (dec.).

Analysis calculated for C$_{20}$H$_{16}$N$_2$O$_2$: C, 75.9; H, 5.07; N, 8.9. Found: C, 76.0; H, 5.2; N, 8.8.

The subject invention thus provides improved methods for the preparation of 1,2,3,4-tetrahydro-7-hydroxyquinoline, 1-alkyl-1,2,3,4-tetrahydro-7-hydroxyquinoline and derivatives thereof, which serve as precursors to novel rhodamine and phenoxazone class of fluorescent dyes. The instant invention also provides improved methods for the preparation of certain rhodamine and phenoxazone class of dyes and some novel rhodamine and phenoxazone dyes, prepared in accordance with the methods of the present invention. The fluorescent dyes produced in accordance with the instant invention are useful as laser dyes, in the preparation of various products which utilize fluorescent dyes such as printing inks, toys, road safety signs, posters, tags and the like and for chemical and biological research, in therapeutic and diagnostic kits and pharmaceutical products where fluorescent dye markers and tags are used.

The foregoing description of the preferred embodiments of the subject invention have been presented for purposes of illustration and description and for a better understanding of the invention. It is not intended to be exhaustive or to limit the invention to the precise form disclosed; and obviously, many modifications and variations are possible in light of the above teaching. The particular embodiments were chosen and described in some detail to best explain the principles of the invention and its practical application to thereby enable others skilled in the relevant art to best utilize the invention in various embodiments and with various modifications as are suited to the particular use contemplated. It is intended that the invention be defined by the claims appended hereto.

What is claimed is:

1. A method for preparing a compound of the Formula I:

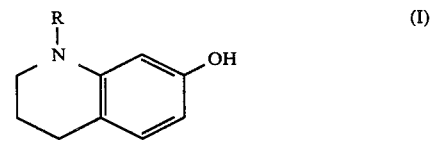

wherein R is hydrogen or linear or branched alkyl of 1 to 10 carbon atoms, comprising the steps of:

(a) treating the compound of the Formula IA

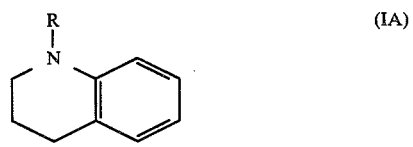

with a sulfonating agent selected from the group consisting of fuming sulfuric acid and acid sulfates at a temperature below about 40° C. by gradual addition of said compound of the Formula IA to an excess of said sulfonating agent to form a 7-sulfonated derivative of IA;

(b) converting said 7-sulfonated derivative to a sulfonate salt; and (c) fusing the product of step (b) with alkaline metal hydroxide.

2. A method according to claim 1 wherein R is alkyl of 1 to 4 carbon atoms.

3. A method according to claim 2 wherein R is methyl.

4. A method for preparing a compound of the Formula I

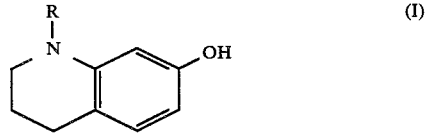

wherein R is a linear or branched alkyl of 1 to 10 carbon atoms, comprising the steps of:

(a) treating quinoline with an alklating agent to form N-alkylated quinoline;

(b) hydrogenating said N-alkylated quinoline to form 1,2,3,4-tetrahydro N-alkyl quinoline;

(c) treating said 1,2,3,4-tetrahydro N-alkyl quinoline from step (b) with a sulfonating agent selected from the group consisting of fuming sulfuric acid and acid sulfates at a temperature below about 40° C. by gradual addition of said tetrahydro N-alkyl quinoline to an excess of said sulfonating agent to form a 7-sulfonated derivative thereof;

(d) converting said 7-sulfonated derivative to a sulfonate salt; and (e) fusing said 7-sulfonated derivative from step (d) with alkaline metal hydroxide.

5. The method of claim 4 wherein said step (b) is conducted utilizing a hydrogenating agent selected from the group consisting of platinum, Raney nickel, sodium borohydride, and tin and HCl.

* * * * *